(12) United States Patent
Gaston, IV et al.

(10) Patent No.: US 6,419,634 B1
(45) Date of Patent: *Jul. 16, 2002

(54) CONDENSATE COLORIMETRIC NITROGEN OXIDE ANALYZER

(75) Inventors: Benjamin M. Gaston, IV, Poway, CA (US); John F. Hunt, Ponte Bedra Beach, FL (US)

(73) Assignee: NitroMed, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,536

(22) Filed: Jan. 31, 2000

Related U.S. Application Data

(63) Continuation of application No. 08/623,643, filed on Mar. 28, 1996, now Pat. No. 6,033,368.

(51) Int. Cl.$^7$ .................................................. A61B 5/00
(52) U.S. Cl. ........................... 600/532; 73/23.3; 422/84
(58) Field of Search ..................... 600/532; 73/23.3; 422/84

(56) References Cited

U.S. PATENT DOCUMENTS

| | | |
|---|---|---|
| 3,373,735 A | 3/1968 | Gallagher |
| 3,544,273 A | 12/1970 | McConnaughey |
| 3,856,051 A | 12/1974 | Bain |
| 3,865,106 A | 2/1975 | Palush |
| 4,446,869 A | 5/1984 | Knodle |
| 4,456,008 A | 6/1984 | Clawson et al. |
| 4,485,822 A | 12/1984 | O'Connor et al. |
| 4,609,537 A | 9/1986 | Tolpin et al. |
| 4,713,095 A | 12/1987 | Ricciardelli |
| 4,821,737 A | 4/1989 | Nelson |
| 4,945,918 A | 8/1990 | Abernathy |
| 5,111,827 A | 5/1992 | Rantala |
| 5,173,264 A | 12/1992 | Zaromb et al. |
| 5,305,762 A | 4/1994 | Acorn et al. |
| 5,361,771 A | 11/1994 | Craine et al. |
| 5,447,165 A  * | 9/1995 | Gustafsson .................. 600/532 |
| 6,033,368 A  * | 3/2000 | Gaston, IV et al. ......... 500/532 |

FOREIGN PATENT DOCUMENTS

| | | |
|---|---|---|
| DE | 9421065 | 5/1995 |
| EP | 0699414 | 3/1996 |
| SU | 1143400 | 3/1985 |

OTHER PUBLICATIONS

Hunt et al, "Condensed Expirate Nitrite As A Home Marker For Acute Asthma," *The Lancet*, 346:1235–1236 (Nov. 4, 1995).

* cited by examiner

*Primary Examiner*—Robert L. Nasser
(74) *Attorney, Agent, or Firm*—Hale and Dorr, LLP

(57) ABSTRACT

Disclosed is a device for determination of the content of higher oxides of nitrogen in exhaled breath condensate which comprises a conduit having an exhalate condensing portion with an inlet and an outlet (the inlet can be configured to fit with a mechanical respirator or, for direct use by the patient, an inlet assembly providing one-way ingress of ambient atmosphere to the device can be associated with the inlet of the conduit exhalate condensing portion); a coolant jacket coaxially surrounding said exhalate condensing portion; a gas release port; and, in enclosed fluid communication with said conduit exhalate condensing portion outlet, a sample assay assembly comprising (i) a translucent analysis chamber attached to the outlet to receive condensate fluid and having a reagent entry port, (ii) a reagent chamber in enclosed fluid communication with the reagent entry port and (iii) a pliable element connecting the outlet and the analysis chamber and forming a portion of the reagent chamber such that flexion of the pliable element closes communication between the outlet and the analysis chamber and contracts the reagent chamber so as to deliver to the analysis chamber controlled amounts of condensate and reagent. The device is disposable and inexpensive, and is used to collect human exhalate for colorimetric assay of liquid and gas phase nitrogen oxides to assist in evaluation of airway inflammation.

28 Claims, 2 Drawing Sheets

CONDENSATE COLORIMETRIC NITROGEN OXIDE ANALYZER

This is a continuation of application Ser. No. 08/623,643, filed Mar. 28, 1996, now U.S. Pat. No. 6,033,368.

FIELD OF THE INVENTION

The invention is directed to a condensate colorimetric nitrogen analyzer oxide that determines the content of nitrogen oxides in exhaled breath condensate.

BACKGROUND OF THE INVENTION

Conventional assessment of severity of airway diseases, including asthma, consists of measures of pulmonary mechanics which are effort dependent and thus not suitable for many pediatric patients, mechanically ventilated patients, or patients with neuromuscular disease. See Crapo R., Pulmonary-function testing. *N. Engl. J. Med.,* 331; 1:25–30; 1994; and American Thoracic Society/European Respiratory Society: Respiratory mechanics in infants— physiologic evaluation in health and disease, *Am. Rev. Respir. Dis.,* 1993; 147:474–96. Currently the Peak Expiratory flow meter is the only method commonly available for home use by asthmatics to monitor the state of their airway disease. This test suffers from being an insensitive indicator of airway inflammation, and is effort dependent. Other physiologic parameters require expensive machines and experienced operators to obtain reproducible results. Klein R., Fritz G. Yeung A., McQuade E., Mansell A., Spirometric Patterns in Childhood Asthma: Peak Flow Compared with Other Indices. *Pediatr. Pulmonol.,* 1995, 20:372–379.

Endogenous production of nitrogen oxide in the human airway has been shown to be increased in patients with asthma and other inflammatory lung diseases. Gaston B., Drazen J., Chee, C., et al. Expired nitric oxide concentrations are elevated in patients with reactive airways disease. *Endothelium.* 1993; 1:S87; Gustafsson, I. E., Leone A. M., Persson M. G., Wiklund N. P., Moncada S., Endogenous nitric oxide is present in the exhaled air of rabbits, guinea pigs and humans. 1991; 181; 2:852–857. However, measurement of gas phase nitric oxide (nitrogen monoxide) per se in the parts per billion range found in the airway requires the use of mass spectrometry or chemiluminescent technology, which are cumbersome, expensive and not reasonably suited for home use.

Moreover, measurement of aqueous phase higher oxides of nitrogen compounds such as S-nitrosothiols, nitrite and nitrate, which are not nitrogen monoxide but which are likewise elevated in concentrations in subjects with inflammatory lung disease, has required that patients be hospitalized for invasive airway sampling procedures, including airway intubation and bronchoalveolar lavage. Gaston, B., Reilly J., Drazen J., et al., Endogenous nitrogen oxides and bronchodilator S-nitrosothiols in human airways. Proc. Natl. Acad. Sci., 1993; 90:10957–10961.

SUMMARY OF THE INVENTION

The invention provides a device for determination of the content of higher oxides of nitrogen in exhaled breath condensate which comprises a conduit having an exhalate condensing portion with an inlet and an outlet (the inlet can be configured to fit with a mechanical respirator or, for direct use by the patient, an inlet assembly providing one-way ingress of ambient atmosphere to the device can be associated with the inlet of the conduit exhalate condensing portion); a coolant jacket coaxially surrounding said exhalate condensing portion; a gas release port; and, in enclosed fluid communication with said conduit exhalate condensing portion outlet, a sample assay assembly comprising (i) an optical analysis chamber, for example, clear or translucent, attached to the outlet to receive condensate fluid and having a reagent entry port (ii) a reagent chamber in enclosed fluid communication with the reagent entry port and (iii) a pliable element connecting the outlet and the analysis chamber and forming a portion of the reagent chamber such that flexion of the pliable element closes communication between the outlet and the analysis chamber and contracts the reagent chamber so as to deliver to the analysis chamber controlled amounts of condensate and reagent. The device is disposable and inexpensive, and is used to collect human exhalate for colorimetric assay of liquid and gas phase nitrogen oxides to assist in evaluation of airway inflammation.

In a preferred embodiment the device further comprises an inlet assembly providing one-way ingress of ambient atmosphere to the exhalate condensing conduit inlet. This is ideal for the patient who is breathing directly into the device, rather than the situation where the device is connected to a mechanical respirator.

In a preferred embodiment the device further comprises, between the inlet assembly and the exhalate condensing conduit portion, a filter capable of removing particulate matter from exhaled air which passes therethrough.

In another preferred embodiment, the device further comprises a coolant material in the coolant jacket.

In another preferred embodiment, the device further comprises a reagent composition capable of detecting a nitrite or nitrate in an exhalation condensate sample.

In another preferred embodiment, the device further comprises a reagent-permeable membrane in the reagent entry port.

In another preferred embodiment, the device further comprises a rupturable membrane in the reagent entry port.

In another preferred embodiment, the inlet assembly further includes therein a filter capable of removing ambient nitrogen oxides from exhalate passing therethrough.

In another preferred embodiment the exhalate condensing conduit portion comprises a single lumen conduit having a lumen diameter sufficient to cause substantially no resistance to the flow of exhalate therethrough.

In another preferred embodiment the exhalate condensing conduit portion comprises a plurality of conduit tubules having a collective lumen diameter sufficient to cause substantially no resistance to the flow of exhalate therethrough.

The purpose of this invention is to condense exhaled lung gas and vapor for aqueous phase nitrogen oxide analyses. This will assist in the evaluation of the human airways' production of nitrogen oxides in both gas and several liquid phase states, including nitrite and nitrate, with potential for multiple other studies to help delineate the lung's redox environment and the airways' degree of inflammation. The investigations which have resulted in the present invention indicate that easily measured liquid phase exhaled nitrogen oxides, nitrite and nitrate, are likewise elevated in asthmatic subjects during periods of inflammation (see abstract enclosed, unpublished data). Utility in the clinical setting for inexpensive and domiciliary evaluation of airway inflammation in various disease states, including asthma, is the primary purpose of the device of the present invention and its utility has been proven, inter alia, as demonstrated herein.

The invention is comprised of cold tolerant materials and consists of two tubing units, one inside the other. Surrounding the inner tube or set of tubes, and contained by the outer tube, is a chemical substance which has a high specific heat, and therefore, once frozen, can maintain freezing temperatures for an extended period of time. The disposable unit can be frozen in a standard size home freezer and then connected together with collection and analysis instruments as a compact integral unit.

Attached to the proximal portion of the unit is a port through which the subject breathes. This consists of two one-way valves which direct atmospheric air or selected gases to the patient's lungs during inspiration, and channel exhaled gas down a condensing tube. Gas moves in only one direction through the condensing apparatus. Inserted between the breathing port's mouthpiece and the condensing chamber is a microporous filter which traps all small particles (such as saliva or sputum), is impermeable to liquids, but allows gas and vaporized fluids of less than 0.3 microns in diameter to pass. This acts as a saliva trap and may also act as a filter for the larger fluid particles which may be aerosolized in the larger airways.

The distal end of the condensing chamber tube(s) is attached to a collecting apparatus which utilizes gravity to trap condensed fluid. At the bottom of this trap is a clear plastic analyzing chamber in which the sample is sequentially warmed, sealed, reacted with colorimetric reagents and analyzed spectrophotometrically by the non-disposable colorimeter.

The patient breathes comfortably in and out through the mouthpiece. Lung fluid vapor collects on the inner surface of the inner tube(s) of the condensing apparatus starting immediately. Gravity carries the larger droplets down the tube, these droplets recruiting other small droplets on their trip to the collecting vial distally. Alternatively, after a fixed period of tidal breathing, the condensed fluid can be expressed down the inner tube with a device similar to a syringe plunger. Aqueous phase nitrite and nitrate can be measured by standard colorimetric assays, and can be reasonably quantified by simple tests performed by patients in their homes.

DETAILED DESCRIPTION OF THE INVENTION

The device of the invention has several advantages, including:

1. This is the only device which measures airway inflammation with a simple home assay, without invasive procedures or expensive and cumbersome testing equipment.

2. Ease of transportability and use of the apparatus.

3. Clinical application for individual patients in their own home or in the clinic or hospital setting to test for or monitor status of asthma or other causes of airway inflammation. May be used to predict disease exacerbations, allowing time for successful early intervention.

4. Clinical applicability in the setting of mechanically ventilated patient to easily monitor airway inflammation.

5. Clinical applicability for measuring airway inflammation in many children too young to cooperate with standard pulmonary function testing, but who can cooperate with tidal breathing through a tube. Similar potential in patients with neuromuscular disease in whom standard tests are uninterpretable.

The device can be made with easily available materials. The cooling substance in the condensing chamber can be water, or a viscous substance with a high specific heat. The device can also be made, as described above, without refrigerant, utilizing a gas/membrane or gas/aqueous reaction compartment.

Figure 1:
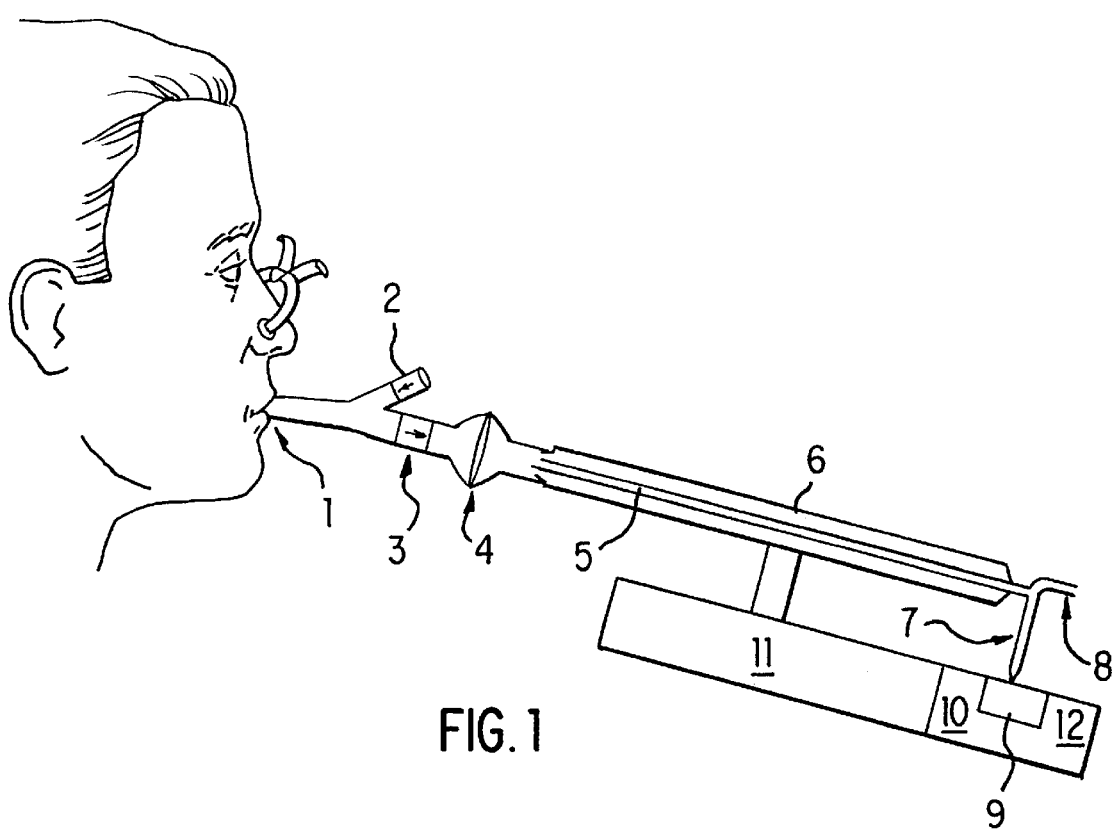
FIG. 1 is a side elevation view, partially in section, of the device of the invention.

Referring now to FIG. 1, mouthpiece 1 is formed as an integral element with low resistance one-way valve 2 allowing inspiration of air into the device of the invention resulting from inhalation through it by the user. Low resistance one-way valve 2 optionally contains potassium permanganate and a charcoal filter to remove ambient nitrogen oxides. Mouthpiece 1 and low resistance one-way valve 2 are further integral with low resistance one-way valve 3 to direct all expired gas from the user into the remaining elements of the device. Integral with and downstream of low resistance one-way valve 3 is low resistance filter 4, containing elements which removes all particulates greater than 0.03 $\mu$M in diameter.

Connected downstream to low resistance filter 4 is condensing chamber 5 which consists of either a single, long inert plastic tube of sufficient diameter to be of low resistance to air expired into the device, or a bundle of shorter, parallel, inert plastic tubes of sufficient number to provide minimal resistance to airflow. Condensing chamber 5 is in continuity with, i.e., receives air arising from filter 4. Coolant chamber or jacket 6 contains an aqueous solution of sufficient osmolality to cause freezing point depression to just above the minimum temperature of the average household freezer, e.g., in a range of ±15° F., preferably below 0° F.

Condensing chamber 5 is completely sealed from exposure to coolant chamber 6. Essentially coolant chamber 6 coaxially surrounds condensing chamber 5 so as to control the temperature within condensing chamber 5. Condensing chamber 5 is continuous with a conduit that divides to condensate delivery conduit 7 and exhaust port 8. A reagent impregnated mesh, such as filter paper, can optionally be situated in condensate delivery conduit 7 for reagent combination with condensate prior to their arrival in sample analysis assembly 9. Exhaust port 8 comprises a one-way, low-resistance valve through which air, in which the condensate has been analyzed, is expelled from the device of the invention.

Sample analysis assembly 9 is connected to the outlet of condensing chamber 5 through condensate delivery conduit 7 and is described in detail with reference to FIG. 2A.

Analyzer 10 which is not a component of the disposable device of the invention, includes a wavelength-filtered light source and photometer bulb, for measuring the specific absorbance of reacted reagent in sample analysis assembly 9, and a computer both for calculating and displaying the corresponding nitrogen oxide content of the sample in sample analysis assembly 9 and for calibrating the absorbance/concentration relationship based on standard samples is shown as an association of conventional elements in essentially block form. Elements 1 through 9 of the device of the present invention form a disposable unit which is stored under refrigeration, preferably frozen, until used. In contrast, analyzer 10 is not disposable and is maintained at room temperature.

The disposable unit comprising elements 1–9 is removed from frozen storage and placed as a unit in connecting housing 11, which is attached to analyzer 10 in such a way that sample analysis assembly 9 fits snugly into connecting housing 11. Connecting housing 11 serves to hold the disposable and non-disposable units together at the appropriate orientation, and to prevent the subject user's hand from becoming affected by the cold of the disposable device while holding the apparatus during gas sampling. Sample analysis assembly 9 is surrounded by a thermostatically controlled heating coil 12 attached to connecting housing 11 and analyzer 10 which brings the sample and test reagents to 25° C. Heating coil 12 is part of the non-disposable unit.

Figure 2A:
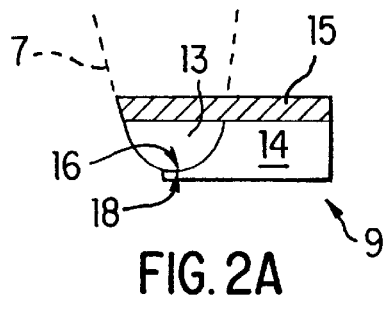
FIG. 2A is a side sectional elevation view of a preferred embodiment of the sample assay assembly of the device with the non-disposable analyzer, and includes a top view of the connecting pincer valve.

Referring now to FIG. 2A, illustrated in hatched line is the outlet of condensate delivery conduit 7, which is in enclosed fluid communication with sample analysis assembly 9. Sample analysis 9 comprises contiguous with a round, hard-plastic clear or translucent analysis chamber 13, a pliable reagent chamber 14 and pliable element 15. Condensate delivery conduit 7 and sample analysis assembly 9 are brought into juxtaposition and are connected by pliable element 15, which is a soft-plastic component that extends beyond the diameter of condensate delivery conduit 7. At the bottom of analysis chamber 13 is an opening 16 in which is positioned a fluid-permeable membrane or a thin, plastic rupturable membrane 18.

Reagent(s) for colorimetric nitrogen oxide salt analysis could be a diazo reagent, or such a reagent in conjunction with nitrate reductase and appropriate cofactors to enable both nitrite and nitrate to be measured simultaneously. Other reactions, such as reduction of nitrite and nitrate to nitric oxide in vanadium chloride, followed by reaction with oxyhemoglobin to achieve a colorimetric shift in the Soret band, and including heterolytic cleavage of S—NO bonds with mercuric chloride followed by diazo analysis could also be employed.

Figure 2B:
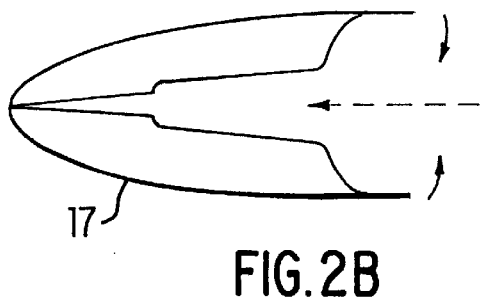
FIG. 2B is a top view of the pincer which flexes the pliable element of the sample assay assembly.

When exhaled, the condensate of exhaled air passed into condensate delivery conduit 7 and then into analysis chamber 13. Thereafter, the user squeezes pliable element 15, using pincer 17 (shown in FIG. 2B). When pincer 17 is closed against pliable element 15, this causes the volume of reagent chamber 14 to decrease such that reagent therein is forced upwardly through the opening 16 and permeable or rupturable membrane into analysis chamber 13 to combine and react with the condensate. Thereafter, the reaction product of this chemical reaction is analyzed by colorimetry using the non-disposable colorimeter which passes a beam of light through a fixed path of analysis chamber 13.

The distal end of the condensing chamber tube(s) 5 is attached to a collecting apparatus comprising condensate delivery conduit 7 which utilized gravity to trap condensed fluid. At the bottom of this trap is flexion element 15 and the clear plastic analysis chamber 13 in which the sample is sequentially warmed, sealed, reacted with colorimetric reagents from reagent chamber 14 and analyzed spectrophotometrically by the non-disposable colorimeter through the analysis chamber 13.

The patient breathes comfortably in and out through the mouthpiece 1. Lung fluid vapor collects on the inner surface of the inner tube(s) 5 of the condensing apparatus starting immediately. Gravity carries the larger droplets down the tube(s) 5, these droplets recruiting other small droplets on their trip to the condensate delivery conduit 7 distally.

Alternatively, after a fixed period of tidal breathing, the condensed fluid can be expressed down the inner tube 5 with a device similar to a syringe plunger. Aqueous phase nitrite and nitrate can be measured by standard colorimetric assays, and can be reasonably quantified by simple tests performed by patients in their homes.

Potential modifications to the system include:

1. Attachment of an assembly distal to the inspiratory portion which would contain a fiber paper through which the saliva free exhalate is channelled. The filter paper would be impregnated with reagents which react with nitrogen oxides and subsequently change color. A patient could breathe through the filter paper for a given period of time and the degree of color change could be measured against a chart or with a small colorimetric device.

2. Direct attachment to the distal end of the condensing chamber of a filter paper impregnated with dried reagents which will react with the aqueous phase nitrogen oxides to yield a change in color of the paper which can easily be measured in a similar fashion to modification #1 above.

3. Direct attachment of a chamber containing liquid reagents through which the exhalate is bubbled, allowing exhaled nitrogen oxides to directly react with reagents, producing a measurable color change.

4. Attachment of a dehumidifying chamber to the inspiratory portion to eliminate environmental liquid phase nitrogen oxides.

EXAMPLE 1
Expired Nitric Oxide During Tidal Breathing in Humans

Recent insights regarding the use of expired nitric oxide (NO.) concentration measurement as an index of airway inflammation cannot be applied to children too young to perform vital capacity (VC) maneuvers. We have therefore developed assays which require only tidal breathing. Sequential colorimetric measurements were made during quiet breathing by reacting dried air expirate (DAE) with Griess reagent under acid conditions. Tidal expired gas NO. production rates ($V_{NO.}$) were also measured by chemiluminescence over 5 minutes using a 765 liter sealed plethysmograph. Eight control subjects and 6 patients with asthma and cystic fibrosis (CF) were studied. DAE NO— was detected in all normal subject samples with mean (±SD) accumulation curve slope=40±17 nmoles/liter/breath (p<0.05 compared with air controls). By comparison, the mean [dissolved nitrogen oxides ($NO_x$)] collected in a precipitation tube (PT) (−80° C.) from size-filtered lung water produced by normal subjects during quiet breathing was 0.8±0.1 $\mu$M. Tidal $V_{NO}$/body surface area (specific $V_{NO.}[V_{NO.SP}]$) was 0.21±0.043 $\mu$l/min/m² in normal subjects. Consistent with previous reports based on VC measurements, patients with asthma had higher $V_{NO.SP}$ (0.31±0.014 $\mu$l/min/m², p<0.01) and PT $NO_x$ (16±4.0 $\mu$M, p<0.005). Further, patients with CF also had high $V_{NO.SP}$ (0.34±0.84 $\mu$l/m²/min, p<0.005). We report for the first time 1) the detection of NO— in expired air through the use of colorimetric assays; 2) the effort-independent detection of $V_{NO_-}$; and 3) increases in these tidal breath concentrations in patients with asthma and CF. We speculate that tidal-breathing based techniques will have clinical utility both as measures of airway inflammation applicable to home use and as effort-independent measures of airway disease in the pediatric pulmonary function laboratory.

EXAMPLE 2
Device Evaluation in Human Clinical Study

Asthma is an inflammatory disease which leads to airway obstruction. Current tests of disease severity are based on measures of obstruction, alterations of which are late findings in asthma exacerbations. Recent studies reveal that expression of inducible nitric oxide synthase (iNOS) is increased in the airway epithelial and inflammatory cells of patients with asthma. The activity of iNOS is known to be reflected in high concentrations of nitric oxide (NO.) gas measured in the expired air of asthmatic subjects. We studied other aqueous phase $NO_x$ in asthmatic aspirate in an effort to develop a simple test for airway inflammation applicable to home use.

Subjects
  6 normal subjects
    no smoking history
    no history of acute, chronic, or recurrent cardiopulmonary, determatologic, gastrointestinal, or neurologic disease.
  13 asthmatic patients
    3 or more episodes of reversible bronchospasm
    I/E ratio<0.5
    $FEV_1/FVC<0.75$ at study entry Methods Saliva free, 0.2 micron particle size-filtered expired vapor was obtained from subjects breathing quietly through a condensing apparatus.

Nitrite ($NO_2$—) was assayed colorimetrically using Griess reagent.

Nitrate ($NO_3$—) was assayed by chemiluminescence after reduction in vanadium chloride.

Statistical Methods

Mean $NO_x$ concentrations were compared using unpaired t-testing. Results are presented as mean, ± standard error. P values of <0.05 were considered significant.

Results

Figure 3:
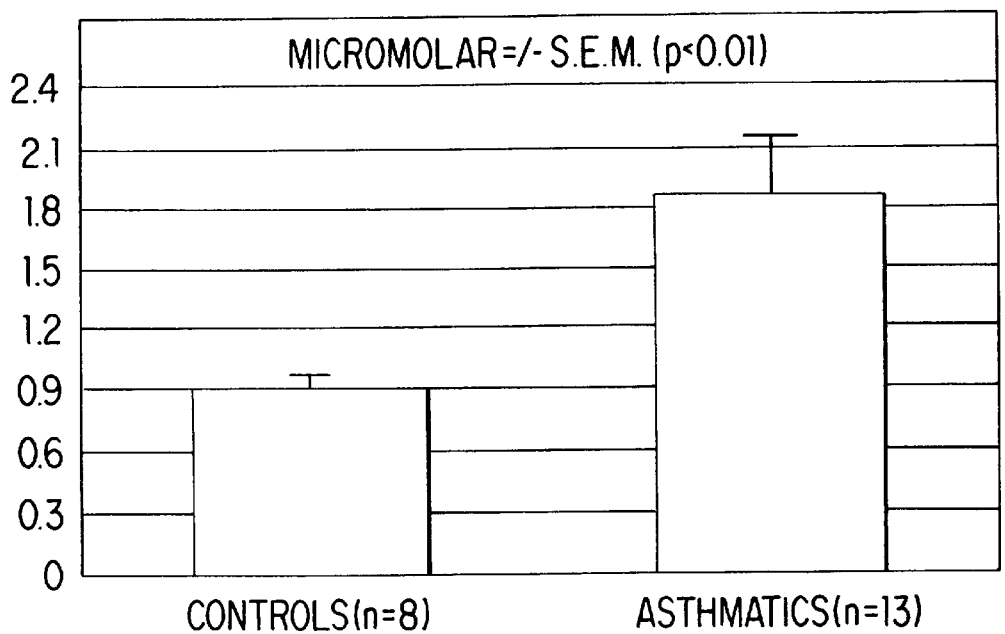
FIG. 3 is a histogram showing the results of the nitrite assay performed as described in Example 2.

As shown in FIG. 3, nitrite concentrations were significantly higher in asthmatic subjects (1.877 μM±0.36) than in controls (0.902 μM±0.08) (p<0.01).

Figure 4:
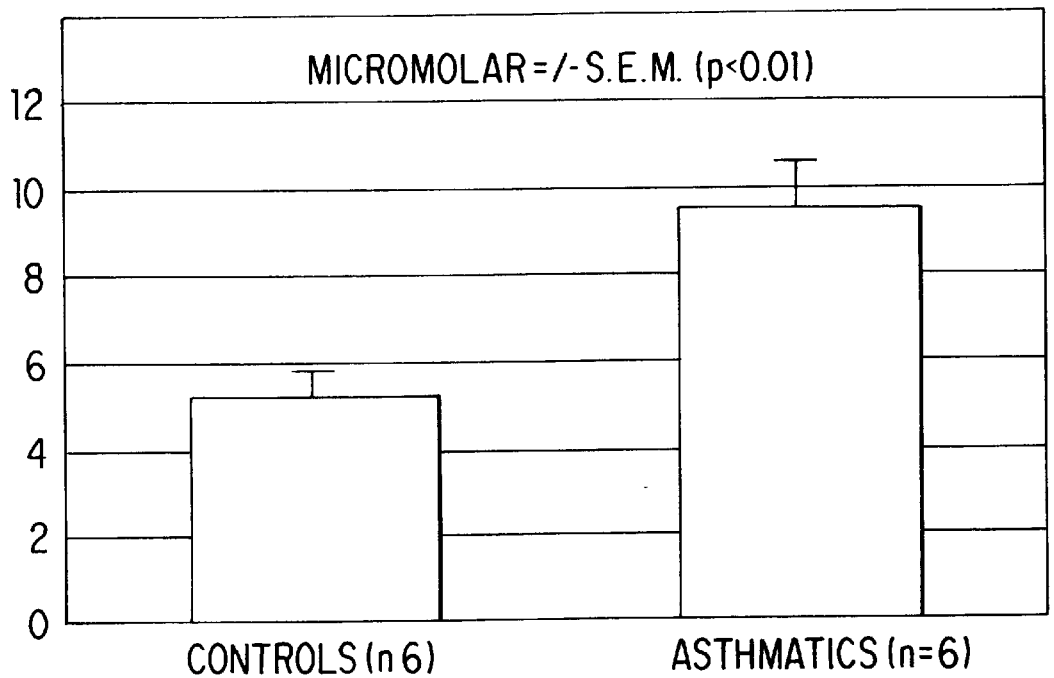
FIG. 4 is a histogram showing the results of the nitrate assay performed as described in Example 2.

As shown in FIG. 4, nitrate concentrations were likewise significantly elevated in asthmatic subjects (9.48 μM±1.25) relative to controls (5.27 μM±0.51) (p<0.01).

Discussion

Tests of airway obstruction, such as the peak flow meter, are currently the primary modality for objectively assessing severity of inflammatory airway disease. These tests have several limitations, including being effort-dependent, and thus are not suitable for many children and neuromuscularly handicapped individuals. They also poorly reflect the degree of underlying inflammation.

Utilizing recent insights regarding the biochemistry of higher oxides of nitrogen, we have developed a simple, non-invasive assay for airway inflammation. Tests such as this could be performed at home, and may prove to be useful in longitudinal evaluation and management of asthma, including dosing of anti-inflammatory medication.

Conclusion

Aqueous phase nitrogen oxides, measured in condensed exhalate, are significantly elevated in asthmatic patients, and can be used to distinguish between normal and inflamed airways.

What is claimed is:

1. A device for determining a content of higher oxides of nitrogen in exhaled breath condensate comprising:
    a conduit for receiving a flow of exhalate, said conduit having an exhalate condensing portion with an inlet, an outlet and a gas release port coupled to the outlet, wherein the inlet comprises a mechanical respirator;
    a coolant jacket coaxially surrounding said exhalate condensing portion; and
    a sample assay assembly in communication with said conduit exhalate condensing portion outlet, wherein the sample assay assembly comprises:
        (i) a light transmissive analysis chamber attached to the outlet to receive the exhaled breath condensate, wherein the light transmissive analysis chamber comprises a reagent entry port,
        (ii) a reagent chamber in communication with the reagent entry port, and
        (iii) a pliable element connecting the outlet and the analysis chamber and forming a portion of the reagent chamber, wherein flexion of the pliable element closes communication between the outlet and the analysis chamber and contracts the reagent chamber to deliver to the analysis chamber controlled amounts of condensate and reagent.

2. The device of claim 1 which further comprises, between the inlet and the exhalate condensing conduit portion, an inlet assembly comprising a filter for removing particulate matter from exhaled air which passes therethrough.

3. The device of claim 1, which further comprises a coolant material in the coolant jacket.

4. The device of claim 1, which further comprises a reagent composition for detecting a nitrite or nitrate in the exhaled breath condensate.

5. The device of claim 1, wherein the reagent entry port comprises a reagent-permeable membrane.

6. The device of claim 1, wherein the reagent entry port comprises a rupturable membrane.

7. The device of claim 1, wherein between the inlet and the outlet is an inlet assembly which further comprises a filter for removing ambient nitrogen oxides from exhalate passing therethrough.

8. The device of claim 1, wherein the exhalate condensing conduit portion comprises a single lumen conduit having a lumen diameter sufficient to cause substantially no resistance to the flow of exhalate theregthrough.

9. The device of claim 1, wherein the exhalate condensing conduit portion comprises a plurality of conduit tubules having a collective lumen diameter sufficient to cause substantially no resistance to the flow of exhalate therethrough.

10. The device of claim 1, which further comprises an inlet assembly between the inlet and the outlet for providing one-way ingress of ambient atmosphere to the exhalate condensing conduit inlet.

11. The device of claim 1, wherein the sample assay assembly comprises a filter paper or fiber paper.

12. The device of claim 11, wherein the filter paper or fiber paper comprises a reagent composition for detecting a nitrite or nitrate in the exhaled breath condensate.

13. The device of claim 1, wherein the sample assay assembly comprises at least one liquid reagent.

14. The device of claim 13, wherein the liquid reagent can detect a nitrite or nitrate in an exhalation condensate sample.

15. A device for determining a content of higher oxides of nitrogen in exhaled breath condensate comprising:
    a conduit for receiving a flow of exhalate, said conduit having an exhalate condensing portion with an inlet, an outlet and a gas release port coupled to the outlet; wherein the inlet comprises a dehumidifying chamber;
    a coolant jacket coaxially surrounding said exhalate condensing portion; and a sample assay assembly in communication with said conduit exhalate condensing portion outlet, wherein the sample assay assembly comprises:
  (i) a light transmissive analysis chamber attached to the outlet to receive the exhaled breath condensate, wherein the light transmissive analysis chamber comprises a reagent entry port,
  (ii) a reagent chamber in communication with the reagent entry port, and
  (iii) a pliable element connecting the outlet and the analysis chamber and forming a portion of the reagent chamber, wherein flexion of the pliable element closes communication between the outlet and the analysis chamber and contracts the reagent chamber to deliver to the analysis chamber controlled amounts of condensate and reagent.

16. The device of claim 15, which further comprises, between the inlet and the exhalate condensing conduit portion, an inlet assembly comprising a filter for removing particulate matter from exhaled air which passes therethrough.

17. The device of claim 15, which further comprises a coolant material in the coolant jacket.

18. The device of claim 15, which further comprises a reagent composition for detecting a nitrite or nitrate in the exhaled breath condensate.

19. The device of claim 15, wherein the reagent entry port comprises a reagent-permeable membrane.

20. The device of claim 15, wherein the reagent entry port comprises a rupturable membrane.

21. The device of claim 15, wherein between the inlet and the outlet is an inlet assembly which further comprises a filter for removing ambient nitrogen oxides from exhalate passing therethrough.

22. The device of claim 15 wherein the exhalate condensing conduit portion comprises a single lumen conduit having a lumen diameter sufficient to cause substantially no resistance to the flow of exhalate theregthrough.

23. The device of claim 15, wherein the exhalate condensing conduit portion comprises a plurality of conduit tubules having a collective lumen diameter sufficient to cause substantially no resistance to the flow of exhalate therethrough.

24. The device of claim 15, which further comprises an inlet assembly between the inlet and the outlet for providing one-way ingress of ambient atmosphere to the exhalate condensing conduit inlet.

25. The device of claim 15, wherein the sample assay assembly comprises a filter paper or fiber paper.

26. The device of claim 25, wherein the filter paper or fiber paper comprises a reagent composition for detecting a nitrite or nitrate in the exhaled breath condensate.

27. The device of claim 15, wherein the sample assay assembly comprises at least one liquid reagent.

28. The device of claim 27, wherein the liquid reagent can detect a nitrite or nitrate in an exhalation condensate sample.

* * * * *